United States Patent [19]

Hornbrook

[11] Patent Number: 5,731,502
[45] Date of Patent: Mar. 24, 1998

[54] INBRED MAIZE LINES CG5NA58 AND CG5NA58A

[75] Inventor: Albert R. Hornbrook, Normal, Ill.

[73] Assignee: Novartis Corporation

[21] Appl. No.: 671,885

[22] Filed: Jun. 28, 1996

[51] Int. Cl.⁶ .............................. A01H 5/00; A01H 4/00; A01H 5/10; C12N 5/04

[52] U.S. Cl. .................. 800/200; 800/235; 800/250; 800/DIG. 56; 435/412; 435/424; 435/430; 435/430.1; 47/58; 47/DIG. 1

[58] Field of Search .................... 800/200, 205, 800/235, 250, DIG. 56; 435/412, 424, 430; 47/58, DIG. 1

*Primary Examiner*—David T. Fox
*Assistant Examiner*—Thanda Wai
*Attorney, Agent, or Firm*—Thomas Hoxie

[57] ABSTRACT

Two inbred maize lines, designated CG5NA58 and CG5NA58A. This invention relates to the plants and seeds of inbred maize lines CG5NA58 and CG5NA58A and to methods for producing maize plants by crossing either inbred line CG5NA58 or CGSNA58A with itself or with another maize line. This invention further relates to hybrid maize seeds and plants produced by crossing either inbred line CG5NA58 or CGSNA58A with another maize line.

34 Claims, No Drawings

INBRED MAIZE LINES CG5NA58 AND CG5NA58A

FIELD OF THE INVENTION

This invention is in the field of hybrid maize (*Zea mays* L.) plant breeding, specifically relating to the inbred maize lines designated CG5NA58 and CG5NA58A.

BACKGROUND OF THE INVENTION

Of all the crops produced by U.S. farmers, maize is the crop that has the most economic value. Maize is utilized as livestock feed, as a basis for human consumption, as raw material for industry and as raw material for the production of ethanol. The primary use of farmer produced field maize is for livestock feed. This includes feed for hogs, beef cattle, dairy cows and poultry.

Human consumption of maize includes direct consumption of sweet maize and as snacks after extruder cooking, ground maize eaten as grits, maize meal and maize flour. Maize oil is also used as a high grade cooking oil, salad oil or in margarine. Maize is used in the production of some starches and syrups. Another important use is in the production of sweeteners used in soft drinks.

The wet-milling and dry-milling processes also produce maize starch and maize flour that have applications in industry. Some of these uses include building materials, the paper industry, textiles and starches.

The seed of inbred maize lines CG5NA58 and CG5NA58A, the plant produced by the inbred seed, hybrid seed produced from the crossing of either inbred to another inbred, the hybrid maize plant grown from said seed, and various parts of the Inbred and hybrid maize plant can be utilized for human food, livestock feed, and as a raw material in the industry.

Maize Breeding

Among the major reasons for the economic importance of maize and the large acreages planted to the crop are the hybridization of the maize plant and the continued improvement, by researchers, of the genetic stock that is used to produce the seed grown by farmers. This process has been on-going since its beginning in the early part of the century. The average bushel per acre yield for the American farmer has gone from around 30 in the middle of the 1930's (before hybrids became dominant) to the present average of close to 120. While not all of this four-fold increase can be attributed to genetic improvement (availability of relatively cheap nitrogen and improvements in farming practices are two other components), a good share of it can.

The physical structure of the maize plant provides the maize breeder with opportunities either to cross a plant with another plant or to self-pollinate a given plant. Since the male inflorescence (the tassel) and the female inflorescence (the ear) are physically separated from each other on the plant, the breeder has the ability to mate plants as desired with ease. Similar physical manipulations are used both for cross-pollinating and for self-pollinating a maize plant. The silks (stigmae of maize female florets) are protected from pollination until pollen is collected from the male inflorescence. For cross-pollination, pollen from one plant is distributed on the silks of another plant, while for self-pollination, pollen from a plant is distributed on silks of the same plant. Sib-pollination is a type of cross-pollination in which both plants are closely related genetically. Cross pollinating and self-pollinating techniques are used in the development of inbreds which, when crossed, produce seed of commercially available maize hybrids. Self-pollination and sib-pollination increase the level of inbreeding in progeny plants, leading to fixation of alleles. With continued inbreeding comes a large reduction in vigor and productivity. This phenomenon is know as inbreeding depression. The progeny from the crossing of two inbred lines is a first generation ($F_1$) hybrid, which has better productivity and agronomic characteristics than either of the inbred parents. This phenomenon is called hybrid vigor or heterosis. Heterosis is reduced markedly in succeeding generations ($F_2$, $F_3$, etc.), making it economically justifiable for the farmer to obtain $F_1$ seed each year for planting. As a result, the hybrid maize seed industry benefits both farmers and producers of hybrid maize seed.

Maize is a highly variable species. For hundreds of years, maize breeding consisted of isolation and selection of open-pollinated varieties. Native Americans evolved many different varieties since the domestication of maize in prehistory. During the course of the nineteenth century, North American farmers and seedsmen developed a wide array of open-pollinated varieties, many of which resulted from an intentional or an accidental cross between two very different types of maize: the Southern Dents, which resemble varieties still grown in Mexico, and the Northern Flints, which seem to have moved from the Guatemalan highlands into the northerly parts of the United States and into Canada. The open-pollinated varieties which were developed during this time were maintained by selection of desirable ears from within the variety for use as foundation seed stock. The only pollination control which was practiced to generate the seed was isolation of the seed crop from pollen from other varieties. Experimentation with inbreeding in open-pollinated varieties showed that it invariably led to a marked reduction in plant vigor and stature, as well as in productivity.

In the early twentieth century, researchers discovered that vigor was restored when a line inbred from an open-pollinated variety was crossed to another, usually unrelated, inbred, and that the resulting hybrids were not only more uniform than open-pollinated varieties, but in many cases were more productive as well. Many of the inbreds developed from open-pollinated varieties were remarkably unproductive, however, which made $F_1$ seed quite expensive to produce in any volume. By the 1930's seedsmen were offering four-way or double crosses to growers. These consisted of a cross between two single crosses, which in turn were each crosses between two inbred lines. In this way, only a small quantity of single cross seed was required, and the seed sold to growers was produced on $F_1$ hybrids. Four-way crosses dominated the seed industry until the late 1950's, when three-way crosses were offered to growers, consisting of seed produced on a single cross hybrid with an inbred line as the pollinator. Through the efforts of public and private maize breeders, inbred lines were selected to be more productive and vigorous than the earlier selections from the open-pollinated varieties, and by the early 1970's, single cross seed was readily available to growers. Presently, the overwhelming majority of hybrid maize seed sold in the United States is single cross seed.

The method of hybridization in maize first involves the development of inbred lines. Inbred lines are commonly developed through some variation of pedigree breeding, wherein the plant breeder maintains the identity of each new line throughout the inbreeding process. To initiate the pedigree breeding process, the breeder may make an $F_1$ cross between two existing inbred lines which complement each other for traits for which improvement is desired, and which cross well with other inbreds from other genetic backgrounds to make commercial hybrids. The $F_1$ is selfed to provide $F_2$ seed, which is planted and selfed to produce the $S_2$ or $F_3$ generation. $S_2$ lines are planted ear-to-row, and self-pollinations are made within individual rows. Rows which do not provide a desirable phenotype are discarded. Selected ears are planted ear-to-row, and this process repeats until substantial homozygosity is attained, usually by the $S_6$ or $S_7$ generation. Once homozygosity is attained, the inbred can be maintained in open-pollinated isolations.

Maize breeders in general structure their efforts to take advantage of known heterotic patterns; that is, they use their knowledge of which inbreds make good hybrids with which other inbreds, and they ensure that genetic material from these heterotic pools does not cross over into opposing pools. A highly successful heterotic pattern in the United States corn belt has been to use lines from a population known as Iowa Stiff Stalk Synthetic crossed with lines having more or less of a Lancaster background to provide hybrids for growers (Lancaster was a relatively unimportant open-pollinated variety, until it was discovered in the early years of inbred/hybrid development that it provided an outstanding source of lines with good general combining ability). Other heterotic patterns have also been developed, primarily for the northern and southern regions of the United States. Breeders have understandably been reluctant to use competitive private company hybrids as source material; because, in such instances, usually it will not be known where derived lines fit in a heterotic pattern (Hallauer et al., "Corn Breeding", *Corn and Corn Improvement* pp. 463–564, (1988). As well, using competitors' hybrids as source germplasm risks the dispersal of existing heterotic patterns: many breeders feel that introducing, for example, Lancaster material into an Iowa Stiff Stalk background would lessen their ability to develop lines which could be crossed to Lancaster-derived inbreds. Unless it is known that a competitor's hybrid was genetically distinct from a breeder's own material, it is considered to be a more risky approach to improvement of a heterotic pool than utilizing known material. When the source population of CG5NA58 was developed, it was not clear that a successful, usable commercial line would have been the result, since it was not known at the time where such an inbred could fit into any heterotic pattern.

Even restricting efforts to known heterotic patterns, a breeder can never be certain that a given cross will provide an improved inbred. The nature of heterosis is not at all well understood. No one knows why, for example, B73×Mo17 was such an advance in productivity over previous hybrids. To say they are heterotic is uninformative: it merely describes what has been observed without explaining the phenomenon. Part of the uncertainty results from the mode of inheritance of many traits of interest, and the mathematics of genetically segregating populations. For example, the trait of chief interest in maize, productivity of marketable grain, is not simply inherited, but instead derives from the action of many genes of relatively small effect. This type of inheritance, known as quantitative inheritance, has been extensively studied from a theoretical standpoint, and certain aspects of the behavior of segregating populations can be mathematically predicted. One finding is that the probability of obtaining a specific homozygous inbred decreases exponentially with the number of segregating loci for a given trait. R. W. Allard (*Principles of Plant Breeding* John Wiley & Sons, New York (1960) p.68) teaches that, from a population segregating at n loci, with each locus having only two variants, $2^n$ homozygous genotypes are possible. Thus, if a source population were segregating at only twenty loci, the probability of obtaining any given inbred genotype from this population is less than one in a million. The probability decreases very quickly with more heterozygous loci. Also, if there are loci with more than two variants, the number of possible homozygotes increases and the probability of retrieving a given inbred genotype decreases. The number of loci which affect the trait of gross productivity has been variously estimated at 10 to 1000. In addition, a breeder must pay attention to agronomic traits such as maturity, stalk quality, root quality, grain quality, resistance to diseases and insects, and many others, some of which appear to be negatively correlated with productivity. The total number of genetic loci in the maize genome has been conservatively estimated to be greater than $10^5$.

The objective of a plant breeder when developing a new inbred line of maize is to combine the highest number of desirable alleles into a single isolate as possible. No parent line contains all desirable alleles at all loci, and the breeder hopes to introgress a higher frequency of favorable alleles into resulting progenies. However, with the current state of the art, a breeder is generally not able to define which allele at any given locus is desirable, and for most traits of interest, he does not have information about which genetic loci are involved in influencing the trait. His primary tool to measure the genotypes of progenies is phenotypic evaluation. The phenotype of a plant is influenced both by its genotype and the environment in which it is grown, so the phenotypic measure of a plant is only an indirect measure of its genotype. When environmental effects are large relative to the genotypic effects, it is said that the trait has low heritability. The breeder must evaluate traits of low heritability in many different environments in order to be reasonably sure that he has an accurate estimate of the genotypic effect. Productivity of marketable grain is such a trait, according to years of breeding experience and numerous scientific publications.

The requirement of evaluating genotypes in different environments places serious restraints on the maize breeder in terms of the number of genotypes the breeder will be able to evaluate. The large number of possible genotypes, coupled with the small sample size from a segregating population, make it uncertain that a breeder will be able to intent a new maize inbred which is a measurable improvement over its parents. The invention of new inbred lines and of new hybrids is extremely important to the companies in the hybrid seed maize industry that have investments in research. Much effort is given to the research and development of these inbreds and hybrids. The breeding and selection of inbred lines is a highly specialized skill. It involves many years of inbreeding, skilled selection, correct statistical testing, and decision making.

Techniques involving the tissue culture of maize cells and plant parts has been developed to the point that it is now possible to regenerate plants from nearly all genotypes, by varying the culture media in which the cells or parts are cultured. Based upon experience with other inbreds with somewhat similar genetic background, it is anticipated that inbred maize lines CG5NA58 and CG5NA58A will readily provide regenerable cells in culture of cells or plant parts.

SUMMARY OF THE INVENTION

According to the invention, there is provided two novel inbred maize lines, designated CG5NA58 and CG5NA58A. This invention thus relates to the seeds of inbred maize lines CG5NA58 and CG5NA58A, to the plants of inbred maize line CG5NA58 and CG5NA58A, and to methods for producing a maize plant produced by crossing the either inbred line CG5NA58 or CG5NA58A with itself or another maize line. This invention further relates to hybrid maize seeds and plants produced by crossing the inbred line either CG5NA58 or CG5NA58A with another maize line.

Definitions

This section will outline the definitions of terms used herein.

The following are traits evaluated in Table 1:
- Plant height is the height from the ground of the point of exsertion from the stalk of the highest ear.
- Ear height is self-explanatory.
- Initial pollen is stated as number of days from planting to the first pollen shed observed in the variety.
- Initial silk is stated as number of days from planting to the first silks observed in the variety.
- Mid pollen is stated both as number of days and as heat units from planting to the date of full pollen shed observed in the variety. Heat units are calculated on a daily basis as ((Maximum temperature in degrees Fahrenheit—Minimum temperature in degrees Fahrenheit)/2)—50, with the constraint that temperatures above 86° F. are counted as 86° F., and temperatures below 50° F. are counted as 50° F.
- Mid silk is stated as number of days and as heat units from planting to the full silking observed in the variety. Heat units are calculated as above.
- Tassel size rating describes the size of the tassel, in which a rating of 1 indicates a large tassel and 9 indicates a small tassel.
- Kernels per kilogram is self-explanatory.
- Percent of large kernels is the percentage of kernels which pass through a 24/64 inch round sizing screen but not through a 21/64 inch round sizing screen.
- Percent of medium kernels is the percentage of kernels which pass through a 21/64 inch round sizing screen but not through an 18/64 inch round sizing screen.
- Percent of small kernels is the percentage of kernels which pass through a 18/64 inch round sizing screen but not through a 33/128 inch round sizing screen.
- Percent of round kernels is the percentage of kernels which do not pass through a 13/64 inch slot sizing screen.
- Percent of discard kernels is the percentage of kernels which pass through a 33/128 inch round sizing screen plus the percentage of kernels which do not pass through a 26/64 inch round sizing screen.
- Number of 80000 kernel units per hectare accounts for yield and and seed sizes, including discard seed.

The following traits are evaluated in Tables 2a through 2d:
- Value. Value is a simple index which takes into account yield of a hybrid maize variety, market price for grain maize, and the cost of drying to storage moisture (15.5%). It is expressed in dollars per acre.
- Yield (Bushels/Acre). Yield in bushels/acre is the actual yield of the grain at harvest adjusted to 15.5% moisture.
- Percent Moisture. The percent moisture is the water content by weight of the grain at harvest.
- Percent Erect. The percent erect, a measure of standability, is the percentage of plant stalks that are not broken below the ear at the time of harvest.
- Percent Erect Push. Another measure of standability, this is the percentage of plant stalks that are not broken below the ear after having been manually pushed.
- Harvest Roots. Harvest roots is a visual rating. It is based on the number of plants that are root-lodged (leaning from the vertical at an approximate 30° angle or greater) at the time of harvest. The ratings range from 1 to 9. a rating of 1 equals no plants root-lodged and a rating of 9 equals all plants root-lodged.
- Percent Dropped Ears. The percent dropped ears is the percentage of plants whose ears have fallen to the ground at the time of harvest.
- Intactness. Intactness is a visual rating based on the percentage of leaf and stalk matter remaining above the top ear at harvest. The ratings range from 1 to 9. A rating of 1 equals all matter remaining (intact) and a rating of 9 equals all matter gone or the stalk broken over just above the ear.
- Percent Green or Staygreen. The percent green is the percentage of the total ear, leaf and stalk matter still green at the time of data collection, approximately physiological maturity.
- Plant height is the height of the plant from the ground to the tip of the tassel.
- Ear height is the height from the ground of the point of exsertion from the stalk of the highest ear.

The following traits are provided in the inbred description:
- Plant height, ear height, number of primary tassel branches, leaf blade width, number of kernel rows, cob color, cob diameter, ear diameter, and ear length are self-explanatory.
- Leaf attitude describes the manner in which leaves of an inbred variety of maize are arrayed on the plant.
- Tassel branch shape describes how the tassel branches are arrayed in the male inflorescence.
- Anthocyanin pigmentation in various plant parts (glumes, glume bands, anthers, silks, leaf sheaths, internodes, brace roots) describes the intensity of red or purple coloration in these plant parts.
- Ear shape describes the amount of taper found in the ears, which can range from no taper (cylindrical shape of the ears), to much taper (conical ears).
- Grain type describes the flintiness of the grain, which can range from fully flint kernel type to floury kernel type.
- Flowering information describes the flowering time relative to appropriate check inbred lines of maize.
- Flowering synchrony describes whether the plants of the inbred typically silk before pollen shed, silk at the same time as pollen shed, or silk after pollen shed.

DETAILED DESCRIPTION OF THE INVENTION

Inbred maize line CG5NA58 and CG5NA58A are yellow dent maize inbred lines with superior characteristics and provide good parental lines in crosses for producing first generation ($F_1$) hybrid maize. Inbred maize lines CG5NA58 and CG5NA58A are proprietary inbreds of Ciba Seeds.

Inbred maize line CG5NA58 was selected for uniformity and agronomic traits using standard pedigree ear-row selection at Bloomington, Ill. and Kaunakakai, Hi. The source population of CG5NA58 was a cross between LH119 and the commercial single cross Pioneer 3358. The inbred was evaluated as a line and in numerous crosses by the Bloomington Research Station and other research stations across the central and southern maize belt. Thus the line was evaluated for general and specific combining ability.

Inbred maize line CG5NA58 is adapted to the central maize belt and can be used advantageously in producing hybrids that are from approximately 105 day relative maturity to 120 day relative maturity based on the Minnesota Relative Maturity Rating System for harvest moisture of the grain. The inbred is a medium tall inbred with medium green leaves. It sheds less than an average quantity of pollen and is preferred as the seed line in hybrid production. With appropriate management of production fields, CG5NA58 may be used as the pollinator in hybrid production. This line produces relatively tall hybrids with high yielding ability for maturity, low grain moisture at harvest, excellent grain quality, excellent stalk quality and average root quality.

Inbred maize line CG5NA58 has shown uniformity and stability for all traits as described in the following variety description information. It has been self-pollinated and ear-rowed a sufficient number of generations with careful attention paid to uniformity of plant type to insure relative homozygosity and phenotypic stability. The line has been increased by hand and in isolated fields with continued observations for uniformity. No variant traits have been observed or are expected in CG5NA58.

Inbred maize line CG5NA58 is slightly taller than average for lines of its flowering maturity, with ear placement approximately one-half the total plant height. It tends to produce slightly more than one ear per plant. The main ear tends to be longer than average for its flowering maturity, usually with fourteen rows of kernels. The ear is slightly tapered from butt to tip. The silk color of CG5NA58 is green, the cob color is pink, and the grain is a bright yellow semi-dent with excellent quality. CG5NA58 flowers relatively late, yet provides low grain moisture compared to other inbreds of its flowering maturity. Silking and pollen shed are synchronous. The leaf color of CG5NA58 is medium green, and the leaf attitude is semi-erect. Leaves are of medium width. The tassel of CG5NA58 has approximately six tassel branches, which are semi-erect with respect to the main tassel axis, and the anthers are pink. Pollen shed is light but adequate. Most green plant parts are typically free of anthocyanin pigmentation except brace roots, which are dark purple.

CG5NA58 is moderately susceptible to northern corn leaf blight Race 1 (*Exserohilum turcicum*): moderately susceptible to southern corn leaf blight (*Bipolaris maydis*), intermediate in resistance to common rust (*Puccinia sorghi*), susceptible to eyespot (*Kabatiella zeae*), resistant to common smut (*Ustilago maydis*), and moderately susceptible to Stewart's wilt and leaf blight (*Erwinia stewartii*).

Inbred maize line CG5NA58A is an ear-to-row selection from CG5NA58. It does not differ phenotypically from CG5NA58 except for two isoenzyme loci, which are heterozygous in CG5NA58 and homozygous in CG5NA58A. The performance of CG5NA58 and CG5NA58A in hybrids is substantially identical.

CG5NA58 is relatively productive as a seed parent, producing predominantly medium round seed. Table 1 compares CG5NA58 with LH132 and FR1064 for production traits. CG5NA58 shares some pedigree background with both these widely used lines, and is expected to be used in a similar way to these inbreds to produce hybrids for commercial sale.

TABLE 1

Agronomic comparisons of CG5NA58 with FR1064 and LH132.

| Trait | CG5NA58 | FR1064 | LH132 | # Locations |
|---|---|---|---|---|
| Plant height (cm) | 180 | 175 | 168 | 4 |
| Ear height (cm) | 69 | 99 | 69 | 4 |
| Initial pollen (days) | 76.4 | 72.6 | 69.9 | 6 |

TABLE 1-continued

Agronomic comparisons of CG5NA58 with FR1064 and LH132.

| Trait | CG5NA58 | FR1064 | LH132 | # Locations |
|---|---|---|---|---|
| Initial silk (days) | 76.6 | 72.7 | 70.1 | 6 |
| Mid pollen (days) | 78.4 | 74.2 | 71.6 | 6 |
| Mid silk (days) | 78.5 | 74.7 | 72.1 | 6 |
| Mid pollen (heat units) | 1608 | 1518 | 1529 | 6 |
| Mid silk (heat units) | 1611 | 1530 | 1541 | 6 |
| Tassel size rating (1 = large, 9 = small) | 6.9 | 5.4 | 5.6 | 4 |
| Kernels per kilogram | 3168 | 3817 | 3542 | 4 |
| Percent of large kernels | 29.0 | 18.7 | 12.0 | 4 |
| Percent of medium kernels | 50.0 | 49.0 | 46.5 | 4 |
| Percent of small kernels | 21.7 | 32.0 | 42.1 | 4 |
| Percent of round kernels | 61.0 | 23.7 | 22.4 | 4 |
| Percent of discard kernels | 5.0 | 9.7 | 9.8 | 4 |
| Number of 80000 kernel units per hectare | 113.6 | 180.3 | 155.6 | 6 |

This invention is also directed to methods for producing a maize plant by crossing a first parent maize plant with a second parent maize plant wherein the first or second maize plant is an inbred maize plant from either inbred CG5NA58 or CG5NA58A. Further, both first and second parent maize plants may be from either inbred line CG5NA58 or CG5NA58A. Thus, any methods using the inbred maize lines CG5NA58 and CG5NA58A are part of the invention, including backcrosses, hybrid breeding, and crosses to populations. Any plants produced using inbred maize lines CG5NA58 or CG5NA58A as a parent are within the scope of this invention. The best use of the inbred maize lines CG5NA58 and CG5NA58A is for the production of first generation ($F_1$) maize hybrid seeds which produce plants with superior characteristics, by crossing either CG5NA58 or CG5NA58A (either as a seed line or as a pollen line) to another, distinct inbred line, both for sale to growers to produce market grain, and for inbreeding and development of improved inbred lines by its proprietors. A second important use of these inbred lines is for the production of inbred seed of CG5NA58 and CG5NA58A, by crossing CG5NA58 with another plant of CG5NA58, or by directly self-pollinating a plant of CG5NA58, by crossing CG5NA58A with another plant of CG5NA58A, or by directly self-pollinating a plant of CG5NA58A.

As used herein, the term "plant" includes plant cells, plant protoplasts, plant cell of tissue culture from which maize plants can be regenerated, plant calli, plant clumps, and plant cells that are intact in plants or parts of plants such as pollen, flowers, kernels, ears, cobs, leaves, husks, stalks, and the like. Thus another aspect of this invention is to provide for cells which upon growth and differentiation produce either the inbred line CG5NA58 or the inbred line CG5NA58A.

The results in Tables 2 compare CG5NA58 hybrids to other Ciba Seeds hybrids, both commercial and experimental. In each comparison, the hybrids have an inbred in common which is not CG5NA58. Each comparison shows the effect of substituting CG5NA58 for a different inbred; in this way, an idea of general combining ability of CG5NA58 relative to a range of other inbreds is obtained. The data were averaged across locations and replications and include experiments grown by Ciba Seeds maize research programs in 1992, 1993, 1994 and 1995.

Table 2a compares a CG5NA58 hybrid with a commercial hybrid for Ciba Seeds. The general background of the common inbred is Mo17. The data show that the CG5NA58 hybrid yields the same as the commercial hybrid, it is drier, and has equivalent stalks, roots and intactness. The CG5NA58 hybrid also has better test weight. The CG5NA58 hybrid is slightly worse for staygreen. The overall value of the CG5NA58 hybrid in comparison with the commercial hybrid is the same, and because of its earlier maturity, the CG5NA58 hybrid would be expected to be grown where the commercial hybrid could not be grown.

TABLE 2a

Comparison of CG5NA58 hybrid 1 with non-CG5NA58 hybrid 2.
Hybrids 1 and 2 have a line of Mo17 background in common which is not CG5NA58.

| Hybrid | Value $/ac | Yield bu/ac | Percent Moist | % Erect Stalks | % Erect Push | Root H Rating | Dropped Ears (%) | Test Wgt/bu | Intact Rating | Percent Green | Pit Hgt Inches | Ear Hgt Inches |
|---|---|---|---|---|---|---|---|---|---|---|---|---|
| 1 | 350.33 | 145.88 | 16.97 | 96.21 | 73.81 | 3.67 | 0.27 | 56.81 | 5.50 | 24.00 | 98.43 | 42.86 |
| 2 | 352.22 | 148.75 | 18.04 | 95.03 | 83.88 | 2.33 | 1.60 | 55.53 | 5.42 | 29.00 | 98.29 | 43.57 |
| # locs. | 19 | 19 | 19 | 13 | 13 | 3 | 8 | 18 | 12 | 5 | 7 | 7 |
| LSD (0.01) | 36.24 | 14.88 | 0.69 | 3.55 | 23.20 | 14.42 | 3.52 | 0.92 | 0.97 | 10.29 | 7.26 | 11.14 |
| LSD (0.05) | 26.45 | 10.86 | 0.50 | 2.54 | 16.55 | 6.25 | 2.38 | 0.67 | 0.69 | 6.21 | 4.79 | 7.36 |
| LSD (0.10) | 21.83 | 8.96 | 0.41 | 2.07 | 13.54 | 4.24 | 1.91 | 0.55 | 0.56 | 4.77 | 3.80 | 5.84 |
| LSD (0.50) | 8.66 | 3.56 | 0.16 | 0.81 | 5.28 | 1.19 | 0.72 | 0.22 | 0.22 | 1.66 | 1.40 | 2.16 |
| Diff. | 1.89 | 2.87 | 1.07 | −1.19 | 10.07 | −1.33 | 1.34 | −1.28 | −0.08 | 5.00 | −0.14 | 0.71 |
| CG5NA58 hybrid is: | same | same | drier | same | same | same | same | better | same | worse | same | same |

Table 2b compares a CG5NA58 hybrid with another commercial hybrid for Ciba Seeds. The general background of the common inbred is early Mo17. The inbred in common differs from that in the comparisons of Table 2a. The CG5NA58 hybrid yields more, has better value, is drier, and has better testweight.

TABLE 2b

Comparison of CG5NA58 hybrid 1 with non-CG5NA58 hybrid 2.
Hybrids 1 and 2 have a line of Mo17 background in common which is not CG5NA58 5n984,4nn51

| Hybrid | Value $/ac | Yield bu/ac | Percent Moist | % Erect Stalks | % Erect Push | Root H Rating | Dropped Ears (%) | Test Wgt/bu | Intact Rating | Percent Green | Pit Hgt Inches | Ear Hgt Inches |
|---|---|---|---|---|---|---|---|---|---|---|---|---|
| 1 | 330.00 | 137.02 | 16.83 | 96.56 | 67.41 | 2.67 | 0.72 | 55.52 | 6.11 | 12.50 | 89.75 | 39.50 |
| 2 | 303.46 | 126.96 | 17.52 | 95.72 | 61.21 | 1.61 | 0.00 | 54.17 | 6.56 | 7.50 | 85.25 | 38.00 |
| # locs. | 15 | 15 | 15 | 12 | 9 | 3 | 8 | 14 | 9 | 2 | 4 | 4 |
| LSD (0.01) | 35.22 | 14.35 | 0.84 | 3.49 | 30.60 | 5.73 | 1.80 | 1.10 | 1.13 | 318.29 | 10.26 | 18.85 |
| LSD (0.05) | 25.38 | 10.34 | 0.60 | 2.47 | 21.03 | 2.48 | 1.22 | 0.79 | 0.78 | 63.53 | 5.59 | 10.27 |
| LSD (0.10) | 20.84 | 8.49 | 0.49 | 2.02 | 16.96 | 1.69 | 0.98 | 0.65 | 0.63 | 31.57 | 4.13 | 7.59 |
| Diff. | −26.54 | −10.06 | 0.69 | −0.85 | −6.20 | −1.00 | −0.72 | −1.35 | 0.44 | −5.00 | −4.50 | −1.50 |
| CG5NA58 hybrid is: | better | better | drier | same | same | same | same | better | same | same | higher | same |

Table 2c compares a CG5NA58 hybrid with an important commercial hybrid for Ciba Seeds. The general background of the common inbred is Oh43 and Mo17. The CG5NA58 hybrid has better value and yield compared to the commercial hybrid, but is slighly wetter. The stalk quality and test weight are better for the CG5NA58 hybrid.

TABLE 2c

Comparison of CG5NA58 hybrid 1 with non-CG5NA58 hybrid 2.
Hybrids 1 and 2 have a line of Oh43 and Mo17 background in common which is not CG5NA58.

| Hybrid | Value $/ac | Yield bu/ac | Percent Moist | % Erect Stalks | % Erect Push | Root H Rating | Dropped Ears (%) | Test Wgt/bu | Intact Rating | Percent Green | Pit Hgt Inches | Ear Hgt Inches |
|---|---|---|---|---|---|---|---|---|---|---|---|---|
| 1 | 376.12 | 158.84 | 18.10 | 95.16 | 81.61 | 2.25 | 0.37 | 56.84 | 4.23 | 34.79 | 99.43 | 44.92 |
| 2 | 369.35 | 154.99 | 17.68 | 94.87 | 72.35 | 1.73 | 0.31 | 56.40 | 4.97 | 22.36 | 94.26 | 45.01 |
| # locs. | 111 | 111 | 112 | 69 | 71 | 33 | 45 | 106 | 67 | 45 | 36 | 36 |

TABLE 2c-continued

Comparison of CG5NA58 hybrid 1 with non-CG5NA58 hybrid 2.
Hybrids 1 and 2 have a line of Oh43 and Mo17 background in common which is not CG5NA58.

| Hybrid | Value $/ac | Yield bu/ac | Percent Moist | % Erect Stalks | % Erect Push | Root H Rating | Dropped Ears (%) | Test Wgt/bu | Intact Rating | Percent Green | Pit Hgt Inches | Ear Hgt Inches |
|---|---|---|---|---|---|---|---|---|---|---|---|---|
| LSD (0.01) | 9.13 | 3.65 | 0.36 | 1.21 | 6.58 | 0.70 | 0.33 | 0.36 | 0.34 | 3.35 | 6.85 | 1.97 |
| LSD (0.05) | 6.90 | 2.76 | 0.27 | 0.91 | 4.95 | 0.52 | 0.25 | 0.27 | 0.25 | 2.50 | 5.11 | 1.47 |
| LSD (0.10) | 5.78 | 2.31 | 0.23 | 0.76 | 4.14 | 0.44 | 0.21 | 0.23 | 0.21 | 2.09 | 4.25 | 1.22 |
| LSD (0.50) | 2.36 | 0.94 | 0.09 | 0.31 | 1.68 | 0.18 | 0.08 | 0.09 | 0.09 | 0.84 | 1.71 | 0.49 |
| Diff. | −6.77 | −3.85 | −0.41 | −0.29 | −9.26 | −0.52 | −0.06 | −0.45 | 0.74 | −12.44 | −5.17 | 0.10 |
| CG5NA58 hybrid is: | better | better | wetter | same | better | worse | same | better | same | better | taller | same |

Table 2d compares a CG5NA58 hybrid with a commercial hybrid for Ciba Seeds. The background of the common inbred is LH82. The CG5NA58 hybrid yields much better than the commercial hybrid, has better value and test weight, is the same moisture, and has much better agronomics.

TABLE 2d

Comparison of CG5NA58 hybrid 1 with non-CG5NA58 hybrid 2.
Hybrids 1 and 2 have a line of LH82 background in common which is not CG5NA58.

| Hybrid | Value $/ac | Yield bu/ac | Percent Moist | % Erect Stalks | % Erect Push | Root H Rating | Dropped Ears (%) | Test Wgt/bu | Intact Rating | Percent Green | Pit Hgt Inches | Ear Hgt Inches |
|---|---|---|---|---|---|---|---|---|---|---|---|---|
| 1 | 408.43 | 176.17 | 19.59 | 96.61 | 74.16 | 2.08 | 0.00 | 57.49 | 4.33 | 39.73 | 89.5 | 40.25 |
| 2 | 380.22 | 164.58 | 19.86 | 95.10 | 51.20 | 1.79 | 0.04 | 56.84 | 6.17 | 22.89 | 83.52 | 38.67 |
| # locs. | 39 | 39 | 39 | 27 | 32 | 12 | 19 | 39 | 39 | 23 | 20 | 20 |
| LSD (0.01) | 17.01 | 6.65 | 0.62 | 2.09 | 13.11 | 1.18 | 0.12 | 0.69 | 0.74 | 7.78 | 3.47 | 3.15 |
| LSD (0.05) | 12.70 | 4.97 | 0.46 | 1.54 | 9.74 | 0.84 | 0.09 | 0.51 | 0.55 | 5.72 | 2.54 | 2.30 |
| LSD (0.10) | 10.58 | 4.13 | 0.39 | 1.28 | 8.10 | 0.68 | 0.07 | 0.43 | 0.46 | 4.74 | 2.10 | 1.90 |
| LSD (0.50) | 4.27 | 1.67 | 0.15 | 0.51 | 3.25 | 0.26 | 0.03 | 0.17 | 0.18 | 1.8 | 0.83 | 0.75 |
| Diff. | −28.20 | 11.59 | 0.27 | −1.50 | −22.96 | −0.29 | 0.04 | −0.64 | 1.84 | −16.84 | −6.00 | 1.57 |
| CG5NA58 hybrid is: | better | better | same | better | better | same | same | better | better | better | taller | same |

Restriction fragment length polymorphisms were assessed in the source population of CG5NA58. Of fifty-one RFLP loci characterized, LH119×Pioneer 3358 was found to be heterozygous at thirty-eight (Table 3). Of these thirty-eight loci, eight have three variants and thirty have two variants. Using Allard's formula, this source material is capable of producing 7,044,820,107,264 distinct homozygous genotypes for the loci characterized, only one of which is CG5NA58. To put this into perspective, if all possible inbred genotypes (considering only the RFLP loci which have been evaluated) from this source population were to be grown at a commercial density, with each genotype represented by only one plant, over 100,000,000 hectares would be filled. It is evident that a person highly trained in the art could start with exactly the same source material, use the same breeding techniques, and develop a new maize inbred, but it would be extremely unlikely to be the same inbred as CG5NA58. Further, given sampling error and the necessity for testing across numerous environments, a skilled breeder can have no assurance that he will be able to develop a commercially usable inbred line at all from this or any other source population, let alone one which shows the distinct advantages of CG5NA58.

TABLE 3

Restriction fragment length polymorphisms of CG5NA58 and its parents.

| Probe | CG5NA58 | LHE136 | P3358 | Frequency of 5NA58 allele in original population |
|---|---|---|---|---|
| B05.47 | DD | BB | DD | 0.50 |
| B05.62 | AA | AA | AD | 0.75 |
| B05.71 | AA | AA | AC | 0.75 |
| B06.32 | CC | CC | CC | 1.00 |
| B07.13 | GG | GG | BG | 0.75 |
| B07.71 | DD | DD | DD | 1.00 |
| B08.15 | CC | CC | BC | 0.75 |
| B14.07 | AA | AA | AE | 0.75 |
| B15.21 | AA | AA | AA | 1.00 |
| B16.06 | FF | FF | DF | 0.75 |
| N053 | DD | EE | CD | 0.25 |
| N110 | CC | CC | AC | 0.75 |
| N120 | CC | DD | CD | 0.25 |
| N223 | CC | DD | CC | 0.50 |
| N235 | DD | DD | DD | 1.00 |
| N238 | DD | DD | DD | 1.00 |
| N247 | EE | EE | EE | 1.00 |
| N252 | BB | EE | BC | 0.25 |
| N256 | DD | DD | CD | 0.75 |
| N262 | FF | FF | HH | 0.50 |
| N264 | EE | AA | EH | 0.25 |
| N266 | BB | DD | BE | 0.25 |

TABLE 3-continued

Restriction fragment length polymorphisms of CG5NA58 and its parents.

| Probe | CG5NA58 | LHE136 | P3358 | Frequency of 5NA58 allele in original population |
|---|---|---|---|---|
| N268 | EE | EE | DE | 0.75 |
| N270 | EE | EE | EE | 1.00 |
| N271 | CC | CC | CC | 1.00 |
| N274 | BB | CC | BB | 0.50 |
| N283 | AA | AA | AA | 1.00 |
| N284 | DD | AA | DD | 0.50 |
| N286 | EE | EE | EE | 1.00 |
| N288 | AA | AA | AG | 0.75 |
| N295 | DD | DD | DH | 0.75 |
| N296 | DD | DD | DG | 0.75 |
| N373 | BB | DD | AB | 0.25 |
| N407 | FF | FF | EF | 0.75 |
| N409 | DD | DD | DG | 0.75 |
| N446 | CC | CC | AC | 0.75 |
| N451 | BB | BB | BB | 1.00 |
| N457 | CC | CC | AE | 0.50 |
| N560 | EE | EE | BE | 0.75 |
| N585 | JJ | BB | JL | 0.25 |
| N600 | BB | BB | BE | 0.75 |
| U019 | CC | AA | CC | 0.50 |
| U032 | AA | AA | AA | 1.00 |
| U048 | HH | HH | CH | 0.75 |
| U058 | DD | DD | DE | 0.75 |
| U060 | CC | CC | AC | 0.75 |
| U084 | CC | CC | CD | 0.75 |
| U089 | DD | BB | DE | 0.25 |
| U090 | CC | BB | BC | 0.25 |
| U130 | BB | BB | BB | 1.00 |
| U166 | CC | AA | CC | 0.50 |

Seeds of inbreds CG5NA58 and CG5NA58A have been placed on deposit at the American Type Culture Collection (ATCC), Rockville, Md., 20852, under deposit accession numbers 97473 (CG5NA58) and 97478 (CG5NA58A) on Mar. 13, 1996.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. An inbred maize line designated CG5NA58 (ATCC Designation 97473).

2. A plant of the inbred maize line designated CG5NA58 of claim 1.

3. Plant parts of the plant of claim 2.

4. The plant parts of claim 3 wherein the plant parts are pollen or seed.

5. Tissue culture of the plant of claim 2.

6. Tissue culture according to claim 5 comprising regenerable cells of a plant part selected from meristematic tissue, anthers, leaves, embryos, pollen, and protoplasts therefrom.

7. A maize plant regenerated from the regenerable cells of a tissue culture according to claim 6 having all of the physiological and morphological characteristics of inbred maize plant CG5NA58 (ATCC Designation 97473).

8. An inbred maize plant with all of the genetic, physiological and morphological characteristics of the inbred maize line designated CG5NA58 (ATCC Designation 97473).

9. A method for producing maize seed comprising crossing a first parent maize plant with a second parent maize plant wherein said first or second parent maize plant is the inbred maize plant having designation CG5NA58 (ATCC Designation 97473) and harvesting the seed produced thereby.

10. The method of claim 9, wherein said first and second parent maize plants are both from the inbred maize line designated CG5NA58.

11. A first generation ($F_1$) maize plant and seed thereof produced by the method of claim 9.

12. A first generation ($F_1$) maize plant and seed thereof produced by the method of claim 10.

13. A first generation ($F_1$) hybrid maize plant and seed thereof produced by crossing a first inbred female maize plant with a second inbred male maize plant, wherein said first or second parent maize plant is the inbred maize plant having the designation CG5NA58 (ATCC Designation 97473).

14. The hybrid maize plant and seed thereof of claim 13, wherein said inbred maize plant having the designation CG5NA58 is the female parent.

15. The hybrid maize plant and seed thereof of claim 13, wherein said inbred maize plant having the designation CG5NA58 is the male parent.

16. A method for producing first generation ($F_1$) hybrid maize seed comprising crossing a first inbred parent maize plant with a second inbred parent maize plant, wherein said first or second parent maize plant is the inbred maize plant having the designation CG5NA58 (ATCC Designation 97473), and harvesting the $F_1$ hybrid seed produced thereby.

17. A first generation ($F_1$) hybrid maize plant and seed thereof produced by growing said hybrid maize seed of claim 16.

18. An inbred maize line designated CG5NA58A (ATCC Designation 97478).

19. A plant or plants of the inbred maize line designated CG5NA58A of claim 18.

20. Plant parts of the plant of claim 18.

21. The plant parts of claim 20 wherein the plant parts are pollen or seed.

22. Tissue culture of the plant of claim 18.

23. Tissue culture according to claim 22 comprising regenerable cells of a plant part selected from meristematic tissue, anthers, leaves, embryos, pollen, and protoplasts therefrom.

24. A maize plant regenerated from the regenerable cells of a tissue culture according to claim 23 having all of the physiological and morphological characteristics of inbred maize plant CG5NA58A (ATCC Designation 97478).

25. An inbred maize plant with all of the genetic, physiological and morphological characteristics of the inbred maize line designated CG5NA58A (ATCC Designation 97478).

26. A method for producing maize seed comprising crossing a first parent maize plant with a second parent maize plant wherein said first or second parent maize plant is the inbred maize plant having designation CG5NA58A (ATCC Designation 97478) and harvesting the seed produced thereby.

27. The method of claim 26, wherein said first and second parent maize plants are both from the inbred maize line designated CG5NA58A.

28. A first generation ($F_1$) maize plant and seed thereof produced by the method of claim 26.

29. A first generation ($F_1$) maize plant and seed thereof produced by the method of claim 27.

30. A first generation ($F_1$) hybrid maize plant and seed thereof produced by crossing a first inbred female maize plant with a second inbred male maize plant, wherein said first or second parent maize plant is the inbred maize plant having the designation CG5NA58A (ATCC Designation 97478).

31. The hybrid maize plant and seed thereof of claim 30, wherein said inbred maize plant having the designation CG5NA58A is the female parent.

32. The hybrid maize plant and seed thereof of claim 30, wherein said inbred maize plant having the designation CG5NA58A is the male parent.

33. A method for producing first generation ($F_1$) hybrid maize seed comprising crossing a first inbred parent maize plant with a second inbred parent maize plant, wherein said first or second parent maize plant is the inbred maize plant having the designation CG5NA58A (ATCC Designation 97478), and harvesting the $F_1$ hybrid seed produced thereby.

34. A first generation ($F_1$) hybrid maize plant and seed thereof produced by growing said hybrid maize seed of claim 33.

* * * * *